United States Patent [19]

DeLuca et al.

[11] 4,224,231
[45] Sep. 23, 1980

[54] DERIVATIVES OF 25-HYDROXYCHOLECALCIFEROL

[75] Inventors: Hector F. DeLuca; Heinrich K. Schnoes; Yoko Tanaka, all of Madison; Joseph B. Alper, Waunakee, all of Wis.

[73] Assignee: Wisconsin Alumni Research Foundation, Madison, Wis.

[21] Appl. No.: 71,972

[22] Filed: Sep. 4, 1979

[51] Int. Cl.$^2$ .............................................. C07J 9/00
[52] U.S. Cl. .................................................. 260/397.2
[58] Field of Search ...................................... 260/397.2

[56] References Cited

U.S. PATENT DOCUMENTS

| 4,028,349 | 6/1977 | Partridge, Jr. et al. ......... 260/397.2 |
| 4,038,272 | 7/1977 | Partridge, Jr. et al. ......... 260/397.2 |

OTHER PUBLICATIONS

"Steroids", vol. 32, No. 4, Nov. 1978, pp. 453-465.

*Primary Examiner*—Elbert L. Roberts
*Attorney, Agent, or Firm*—Howard W. Bremer

[57] ABSTRACT

Compounds having the formula

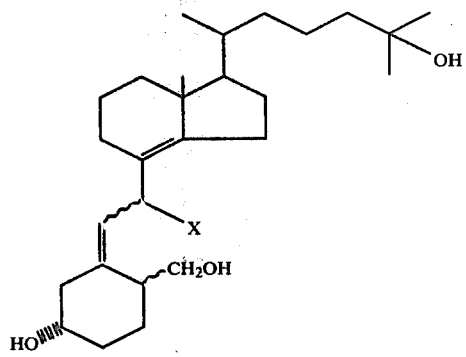

where X is selected from keto or hydroxy.

The compounds are characterized by vitamin D-like activity and would find application in the treatment of disease states where adverse calcium-phosphorous balance or behavior is encountered.

2 Claims, No Drawings

DERIVATIVES OF 25-HYDROXYCHOLECALCIFEROL

The invention described herein was made in the course of work under a grant or award from the Department of Health, Education, and Welfare.

DESCRIPTION

1. Technical Field

This invention relates to a compound which is characterized by vitamin D-like activity.

More specifically this invention relates to a derivative of vitamin $D_3$.

Vitamin $D_3$ is a well-known agent for the control of calcium and phosphorous homeostasis. In the normal animal or human this compound is known to stimulate intestinal calcium transport and bone-calcium mobilization and is effective in preventing rickets.

It is also now well known that to be effective vitamin $D_3$ must be converted in vivo to its hydroxylated forms. For example, the vitamin is first hydroxylated in the liver to form 25-hydroxy vitamin $D_3$ and is further hydroxylated in the kidney to produce $1\alpha,25$-dihydroxy vitamin $D_3$ or 24,25-dihydroxy vitamin $D_3$. The $1\alpha$-hydroxylated form of the vitamin is generally considered to be the physiologically active or hormonal form of the vitamin and to be responsible for what are termed the vitamin D-like activities, such as increasing intestinal absorption of calcium and phosphate, mobilizing bone mineral, and retaining calcium in the kidneys.

2. Background Art

References to various vitamin D derivatives are extant in the patent and other literature. See, for example, U.S. Pat. Nos.: 3,565,924 directed to 25-hydroxycholecalciferol; 3,697,559 directed to 1,25-dihydroxycholecalciferol; U.S. Pat. No. 3,741,996 directed to $1\alpha$-hydroxycholecalciferol; U.S. Pat. No. 3,907,843 directed to $1\alpha$-hydroxyergocalciferol; U.S. Pat. No. 3,715,374 directed to 24,25-dihydroxycholecalciferol; U.S. Pat. No. 3,739,001 directed to 25,26-dihydroxycholecalciferol; U.S. Pat. No. 3,786,062 directed to 22-dehydro-25-hydroxycholecalciferol; U.S. Pat. No. 3,847,955 directed to 1,24,25-trihydroxycholecalciferol; U.S. Pat. No. 3,906,014 directed to 3-deoxy-$1\alpha$-hydroxycholecalciferol; U.S. Pat. No. 4,069,321 directed to the preparation of various side chain fluorinated vitamin $D_3$ derivatives and side chain fluorinated dihydrotrachysterol$_3$ analogs.

DISCLOSURE OF INVENTION

A new derivative of vitamin $D_3$ has now been found which expresses excellent vitamin D-like activity and which, therefore, could serve as a substitute for vitamin $D_3$ in its various known applications and would be useful in the treatment of various diseases such as osteomalacia, osteodystrophy and hypoparathyroidism. This derivative is $3\beta,19,25$-trihydroxy-9,10-secocholesta-5,8(14)-dien-7-one. Its structure is shown below.

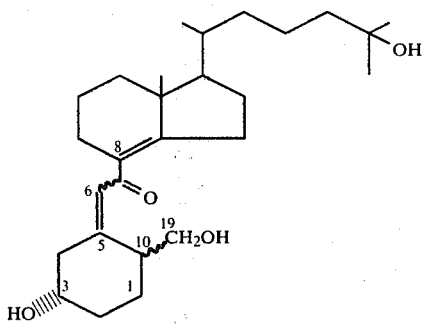

Best Mode for Carrying Out the Invention

The new vitamin D derivative of this invention (compound I, above) was produced from 25-hydroxycholecalciferol (25-hydroxy vitamin $D_3$) as the starting material by in vitro incubation of 25-hydroxycholecalciferol with a kidney homogenate. The incubation yields a mixture of products from which this vitamin D derivative can be readily isolated and purified by chromatography. The structure of the product was established by spectrochemical techniques.

The preparation, isolation and characterization of this novel vitamin D derivative is more fully described in the following examples.

EXAMPLE 1

Preparation of Kidney Homogenate and Incubation Media

Five male albino rats, 150–175 g each, were decapitated and the kidneys were removed. A 5% (w/v) kidney homogenate was prepared in cold 0.25 M sucrose; using a Teflon/glass tissue homogenizer. The homogenate was centrifuged at $8000 \times g$ for 15 minutes; the supernatant was decanted and saved.

A buffer solution was prepared that consisted of potassium phosphate buffer, pH 7.4, 200 mM; glucose-6-phosphate, 22.4 mM; ATP, 20 mM; nicotinamide, 160 mM; and NADP, 0.40 mN. The pH was readjusted to 7.4 with 2 N KOH.

A salt solution was prepared consisting of 5 mM $MgCl_2$, 100 mM KCl, and 10 units of glucose-6-phosphate dehydrogenase in 20 ml of distilled water.

EXAMPLE 2

Incubation of 25-hydroxycholecalciferol with Kidney Homogenate

Five ml of homogenate supernatant, 2.5 ml of buffer, and 2.5 ml of salt solution (all prepared as described above) were combined in a 125 ml Erlenmeyer flask. This mixture was flushed with $O_2$ for 30 seconds. Three-hundred micrograms of 25-hydroxy vitamin $D_3$ in 100 $\mu$l of ethanol were then added and the flask was capped. Thirty such flasks were prepared and were incubated for two hours with shaking (120 oscillations per minute) at 37° C. The contents of the flasks were then poured into 1500 ml of dichloromethane in a 2 liter separatory funnel; the flasks were rinsed once with dichloromethane. The resulting biphasic mixture was agitated for five minutes, followed by removal of the organic phase. The remaining aqueous phase was reextracted with 1500 ml dichloromethane. The combined organic phases were then concentrated in vacuo to ca. 100 ml, and this solution was refrigerated overnight. The resulting precipitate was removed by filtration and the solvent was removed in vacuo.

EXAMPLE 3

Isolation and Purification of Product

Evaporation of the dichloromethane extract (as obtained in Example 2) left a yellow oil, which was dissolved in 0.5 ml of chloroform/hexane (65/35, v/v) and chromatographed on a 0.7×14 cm Sephadex LH-20 (Sephadex LH-20 is a hydroxypropyl ether derivative of a polydextran marketed by Pharmacia Fine Chemicals, In., Piscataway, N.J.) column packed in the same solvent. The first 11 ml of eluant was discarded and the next 25 ml was collected. The solvent was removed in vacuo and the resulting oil was dissolved in 0.5 ml hexane/chloroform/methanol (9/1/1). This was chromatographed on a 0.7×15 cm Sephadex LH-20 column, packed in and developed with hexane/chloroform/methanol, 9/1/1. The first 9 ml of eluant was discarded and the next 20 ml was collected; the solvents were removed in vacuo to give a clear oil.

The clear oil was dissolved in 150 μl of 9% 2-propanol/hexane and chromatographed on a 4.6×250 mm Zorbax-SIL (a product of Dupont Co., Wilmington, Del.) straight phase high pressure liquid chromatograph column fitted on a Model ALC/GPC-204 liquid chromatograph (Waters Associates, Milford, Mass.); eluant was monitored for absorbance at 254 nm. The solvent system, 9% 2-propanol/hexane at a flow rate of 1.5 ml/min, eluted the derived product (compound I above) between 41–45 ml. After evaporation of the solvent the sample was redissolved in 150 μl methanol/water, 70/30. This was chromatographed on a 9.4×250 nm Zorbax-ODS (octadecylsilane bonded to silia beads available through the Dupont Co., Wilmington, Del.) reversed phase high pressure liquid chromatograph column using methanol/water, 80/20 as the eluant at a flow rate, of 2.0 ml/min. The desired product (compound I) eluted between 47–49 ml; these factions were collected and solvent evaporated under a stream of nitrogen. The compound was redissolved in 100 μl of 9% 2-propanol/hexane and was rechromatographed as above. This gave pure product.

Characterization of Product

The UV absorption spectrum of the product in absolute methanol, exhibited a $\lambda_{max}=249$ nm and a $\lambda_{min}=222$ nm. This indicated that the vitamin D triene chromophore had been modified. When the UV spectrum was taken in ether, the $\lambda_{max}$ was shifted to 253 nm, indicative of an $\alpha,\beta$ unsaturated ketone.

The presence of an $\alpha,\beta$-unsaturated ketone was confirmed by reduction of the product with sodium borohydride which yielded a derivative showing no absorption at 249 nm as expected for reduction of the keto to the corresponding alcohol having the formula:

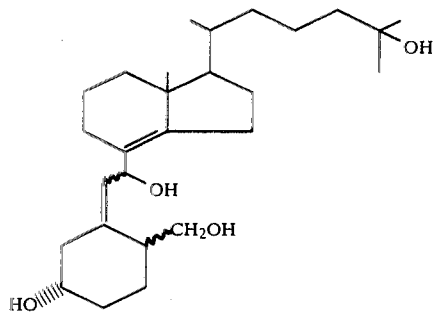

The high resolution mass spectrum of the isolated product (ketone) exhibited high mass peaks at m/e 414.3178 (which corresponds to the composition $C_{27}H_{42}O_3$) and m/e 402.3140 ($C_{26}H_{42}O_3$). This result indicated the true molecular ion of the product to be 432 ($C_{27}H_{44}O_4$) which by loss of $H_2O$ and $CH_2O$ respectively gives rise to the peaks at 414 and 402. Since the starting material, 25-hydroxycholecalciferol, has the composition $C_{27}H_{44}O_2$, the mass spectral results indicated the presence of two additional oxygen atoms in the product. The sequence of peaks at m/e 414, 396 and 378 and at m/e 402, 384 and 366, confirmed the postulated molecular ion at m/e 432 and also indicated the presence of three hydroxy groups in the molecule. The fourth oxygen could then be assigned to the unsaturated ketone function. A peak of m/e 273, corresponding to $H^+$—$C_8H_{17}O$—$CH_2O$, and a peak at m/e 59 ($C_3H_7O$, representing C—25,26,27+hydroxyl) indicated that the product had the same side chain as its precursor, but the absence of the typical vitamin D ring A fragments indicated a highly modified triene system. Given the presence of an $\alpha,\beta$-unsaturated keto (UV spectrum) the unusual elimination of $CH_2O$ in the mass spectrum, could be rationalized by assuming a 7-keto-5-en-10 hydroxymethyl system, a structural arrangement which allows for the loss of the hydroxymethyl group as $CH_2O$ by the well-known McLafferty-rearrangement process.

The high resolution nuclear magnetic resonance spectrum (270 MHz, in $CDCl_3$) of the compound provided conclusive proof of structure. A one proton singlet was observed at δ5.26, as the only signal in the olephinic proton region (δ5-7). Thus, there is only one isolated olefinic proton. Two one-proton doublet of doublets at δ3.62 and δ3.39, with coupling constants of 14 and 7 Hz establish the presence of a 10-hydroxymethyl function (C-19). These signals represent the protons on C-19, coupled to each other (14 Hz) and to a third proton at C-10 (7 Hz) in a typical ABX pattern. Decoupling experiments employing difference double resonance spectroscopy, fully confirmed this structural assignment. A resonance at δ3.6 for the 3α-carbinyl proton and the sharp singlet at δ1.21 for the C-26,27 methyl groups confirm the presence of the 3β-hydroxy and 25-hydroxy function, respectively. The composition of the molecule ($C_{27}H_{44}O_4$) requires two double bonds, one of which can be assigned to the C-5,6-position, thus accounting for the isolated olefinic proton singlet at δ5.26. The other double bond, therefore, has no protons, i.e., is tetrasubstituted, and must be assigned to C-8, 14.

These results in combination establish structure I shown above for the new vitamin D derivative.

Biological Activity of the New Vitamin D Derivative (Compound I)

Male rats (Holtzman Co., Madison, Wis.) were housed in wire cages and given food and water ad libitum for 4 weeks. They were fed a low-calcium vitamin D-deficient diet described by Suda et al (J. Nutr. 100, 1049–1050, 1970). The rats were then divided into three groups of 5–9 animals each and dosed intrajugularly with the test substances. One group received 0.1 ml of ethanol (negative control group), the second received 1,25-dihydroxycholecalciferol (1,25-$(OH)_2D_3$) in 0.1 ml ethanol (positive control group) and the third received the new vitamin D derivative (compound I) in 0.1 ml of ethanol. Amounts are indicated in the table below. Twenty-four hours after dosing, the rats were killed, their blood was collected and their small intestine was removed.

Bone calcium mobilization activity was assayed by measuring the rise in serum calcium levels in response to test compound administered. The collected blood was centrifuged, and a 0.1 ml aliquot of the serum obtained was diluted with 1.9 ml of a 0.1% lanthanum chloride solution. Serum calcium concentrations were determined with an atomic absorption spectrometer Model 403 (Perkin-Elmer Corporation, Norwalk, Conn.). Results are tabulated below.

Intestinal calcium transport activity was determined by a modification of the technique of Martin and DeLuca (Arch. Biochem. Biophys. 134, 139–148, 1969). Results are tabulated below.

| Compound Administered | Ca transport activity | Serum Ca |
|---|---|---|
| | $\mu$moles$^{45}$Ca transported/ cm$^2$ intestine (number of animals) | mg/100 ml (number of animals) |
| 0.1 ml ethanol | 82.3 ± 15.6 (9) | 3.9 ± 0.7 (9) |
| 1,25-$(OH)_2D_3$ (125 ng) | 145.2 ± 47.8 (8) $p < 0.005$ | 5.2 ± 0.5 (8) $p < 0.001$ |
| compound I (500 ng) | 118.5 ± 25.3 (5) $p < 0.0075$ | 5.0 ± 0.4 (6) $p < 0.01$ |

The new vitamin D derivative (compound I) thus shows highly significant vitamin D-like activity in stimulating calcium transport in intestine and mobilizing calcium from bone. Its activity is, in fact, similar to that shown by 1,25-$(OH)_2D_3$, the most potent known metabolite of vitamin D.

Similar activity would be expected for the hydroxy derivative, compound II.

What is claimed is:

1. Compounds having the formula

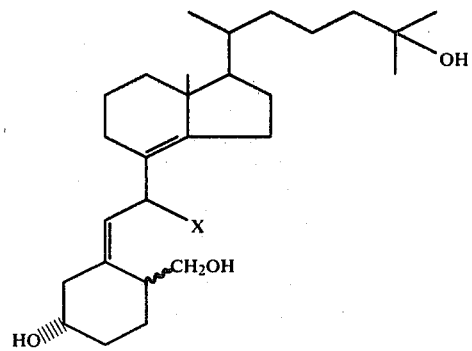

where X is selected from keto or hydroxy.

2. A compound of the formula

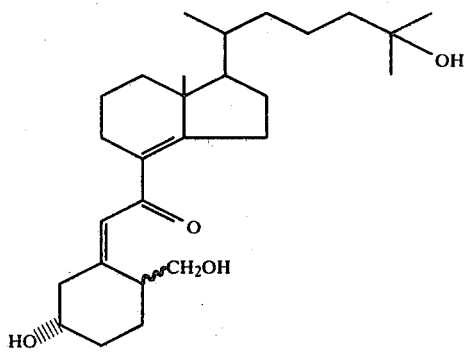

* * * * *